United States Patent
Axelsson

(10) Patent No.: US 6,282,949 B1
(45) Date of Patent: Sep. 4, 2001

(54) APPARATUS FOR DETECTION OF INHOMOGENEITIES IN A LIQUID FLOW

(75) Inventor: Kåge Axelsson, Uppsala (SE)

(73) Assignee: Amersham Pharmacia Biotech AB, Uppsala (SE)

(*) Notice: Subject to any disclaimer, the term of this patent is extended or adjusted under 35 U.S.C. 154(b) by 0 days.

(21) Appl. No.: 09/380,108

(22) PCT Filed: Mar. 10, 1998

(86) PCT No.: PCT/SE98/00419

§ 371 Date: Jan. 24, 2000

§ 102(e) Date: Jan. 24, 2000

(87) PCT Pub. No.: WO98/40733

PCT Pub. Date: Sep. 17, 1998

(30) Foreign Application Priority Data

Mar. 10, 1997 (SE) .................................... 9700853

(51) Int. Cl.⁷ .................................... G01N 29/02
(52) U.S. Cl. .................... 73/64.53; 73/19.03; 73/61.79
(58) Field of Search .................. 73/19.03, 61.75, 73/61.79, 64.53

(56) References Cited

U.S. PATENT DOCUMENTS 3,921,622 * 11/1975 Cole .......................... 73/61.79 X
4,418,565 * 12/1983 St.John ......................... 73/19.03
4,607,520 * 8/1986 Dam .......................... 73/61.79 X
4,651,555 * 3/1987 Dam ............................. 73/19.03
5,394,732 * 3/1995 Johnson et al. ............ 73/19.03 X

FOREIGN PATENT DOCUMENTS 58-131555 * 8/1983 (JP) ............................ 73/61.79

* cited by examiner

Primary Examiner—Daniel S. Larkin
(74) Attorney, Agent, or Firm—Royal N. Ronning, Jr.

(57) ABSTRACT

An apparatus for detecting gas bubbles, in a liquid flow, comprises a one-piece housing (1) of a material that is transmissive to ultrasound, a liquid passage (2) extending through the housing (1), inlet and outlet means on the housing (1) for connecting the liquid passage (2) to the liquid flow, and ultrasonic transducer means (3, 4) on the housing on each side of the liquid passage (2), one transducer means being arranged as sender and the other transducer means being arranged as receiver, with the liquid passage (2) positioned in the sound transmission path between the sender and the receiver, whereby inhomogeneities in the liquid flow can be detected based on the emitted ultrasound energy that is received by the receiver. The housing (1) has two opposed recesses (6, 7), one on the sender side of the liquid passage (2) and one on the receiver side thereof, which recesses in a direction perpendicular to the sound transmission path as well as to the liquid passage.

5 Claims, 1 Drawing Sheet

APPARATUS FOR DETECTION OF INHOMOGENEITIES IN A LIQUID FLOW

TECHNICAL FIELD

The present invention relates to an apparatus for detecting inhomogeneities in a liquid flow, particularly air bubbles, by means of ultrasonics.

BACKGROUND OF THE INVENTION

In many situations it is important to be able to detect the presence of inhomogeneities, such as bubbles, in a liquid flow. This is the case in, for example, the medical field in parenteral administration of treatment solutions where the patient must be protected from the infusion of air bubbles. In industry, for example, the presence of bubbles in a cooling system indicates insufficient cooling capacity. In the analytical field, particularly the detection of air bubbles in passages for liquid chromatography may be mentioned.

A common method for detecting bubbles of gas in a liquid flow is based on the use of ultrasonics and relies on the fact that a gas has a considerably higher acoustic impedance than that of a liquid or a solid material. Thus, if ultrasound is emitted from a sender on one side of a liquid conduit to a receiver on the other side of the conduit, the presence of air bubbles, for example, in the liquid may be detected as a distinct reduction of the received sound energy compared to when there is only liquid in the conduit.

Ultrasound may be generated in a piezoelectric transducer, so-called piezotransducer, in which a crystal is oscillated when actuated by an electric voltage. Conversely, the crystal produces an electric voltage when ultrasound hits the crystal. An ultrasonic transducer may consequently both emit and receive sound.

There is previously known for liquid chromatography purposes an apparatus for bubble detection, which apparatus can be connected to a chromatography system and comprises a plastic block having a liquid through-passage, and a sender and a receiver mounted to either side of the liquid passage. A disadvantage of this apparatus is that the difference between the signals obtained for liquid and air, respectively, is not very great since the emitted ultrasound can propagate beside the liquid passage and still hit the receiver. Likewise, ultrasound that has passed through the liquid passage can then propagate beside the receiver. The apparatus therefore requires complicated electronics for processing the signal from the ultrasound transducers as well as a complicated trimming procedure when installing the device.

U.S. Pat. No. 4,418,565 describes an ultrasonic bubble detection apparatus in the form of a plastic block having inserted therein a pair of opposed ultrasonic transducers (transmitter and receiver) and a channel defined between the transducers, into which channel the liquid conduit where bubbles are to be detected is applied, typically, a tube from a bag or bottle for parenteral administration of solution. Between each transducer and the passage there is a recess filled with an elastomeric ultrasound-transmitting material. To prevent propagation of ultrasound from the sender to the receiver by a route other than through the elastomeric material, and thereby through the liquid conduit, an air-containing slot is positioned in the bottom of the channel. This slot, which is too narrow to be capable of receiving the liquid conduit, extends to a depth at least below the lower edges of the ultrasonic transducers.

While this construction for guiding the ultrasound by shielding at least partially overcomes the above mentioned detection problems of the first described bubble detecting apparatus, the construction has other disadvantages. First of all, the apparatus itself has a complicated construction and contains inter alia screws, spacer elements, and pressure plates. Further, the sensing of a tube is unpractical and requires that the tube be mounted with good acoustic coupling. This may in fact be accomplished if the tube is flexible, but such a tube does not withstand the relatively high fluid pressures that often prevail in, for example, liquid chromatography. The achievement of sufficient acoustic coupling with a rigid tube, on the other hand, requires the use of mounting paste which is very impractical. Due to the slot defined below the liquid conduit channel, the bubble detection apparatus also obtains bad strength properties, especially with regard to twisting or torsional strength.

SUMMARY OF THE INVENTION

One object of the present invention is to provide an ultrasonic apparatus for the detection of gas bubbles and other inhomogeneities in a liquid flow, which apparatus like the first described apparatus above has an integral pressure-resistant liquid passage but where the liquid passage is a dominating element in the sound path in order to insure a great difference between the signal for gas and that for liquid.

Another object of the invention is to provide an apparatus that permits the use of simple electronics for driving and signal processing.

Yet another object of the invention is to provide an apparatus of the type mentioned above which is robust and simple to use.

A further object of the invention is to provide an apparatus of the type mentioned above which contains few details and is simple to manufacture.

According to the invention, these and other objects and advantages are achieved, in an ultrasonic bubble detection apparatus having a one-piece housing with a liquid through-passage and two opposed ultrasonic transducers mounted on the housing on either side of the passage, by the provision of two opposed recesses cut in the housing between each transducer and the liquid passage and on opposite sides of the sound transmission path for the recesses to together shield the sound path between the transducers so that essentially all ultrasonic energy that is received by the receiver has passed through the liquid passage. In other words, the sound distribution between the passage and the surrounding material in the transverse direction of the sound will be such that the passage dominates the cross-sectional area that the ultrasound passes when propagating through the housing. Thereby, a great and reliable difference between air indication and liquid indication is achieved. Due to the opposed arrangement of the recesses, excellent strength of the housing may also be maintained.

One aspect of the invention therefore relates to an apparatus for detecting inhomogeneities in a liquid flow, which apparatus comprises a one-piece housing of a material that is transmissive to ultrasound, a liquid passage extending through the housing, inlet and outlet means on the housing for connecting the liquid passage to the liquid flow, and ultrasonic transducer means on the housing on each side of the liquid passage, one transducer being arranged as sender and the other as receiver with the liquid passage positioned in the sound transmission path between the sender and the receiver, whereby inhomogeneities in the liquid flow can be detected based on the ultrasound energy received by the receiver. The apparatus is characterized in that the housing has two opposed recesses, one on the sender side of the liquid passage and one on the receiver side thereof. In a direction perpendicular to the sound transmission path as well as to the liquid passage, the two recesses extend on opposite sides of the sound transmission path substantially to the level of the respective outer edge of the liquid passage in order to together, by shielding, guide the ultrasound transmission between the sending transducer means and the receiving transducer means so that the ultrasound transmission takes place substantially through the liquid passage (and not through the surrounding material).

In another aspect, the invention relates to a system for detecting inhomogeneities in a liquid flow, which system in addition to the apparatus described above includes means for processing and presenting the signal from the ultrasonic transducers.

To facilitate the understanding of the invention, it is described in more detail below, by way of example only, with regard to a specific embodiment, reference being made to the accompanying drawings.

DETAILED DESCRIPTION OF THE INVENTION

Figure 1:
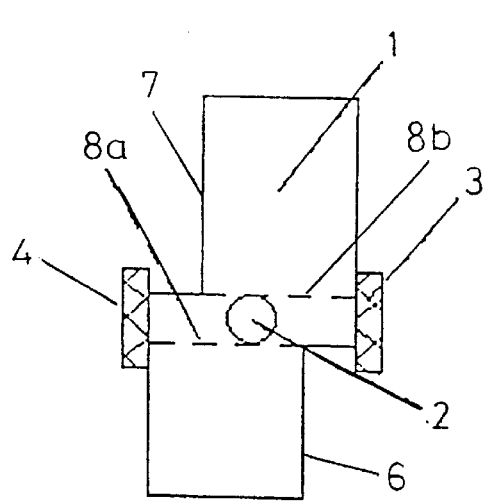
FIG. 1 is a schematic sectional view of an embodiment of the apparatus according to the invention.
Figure 2:
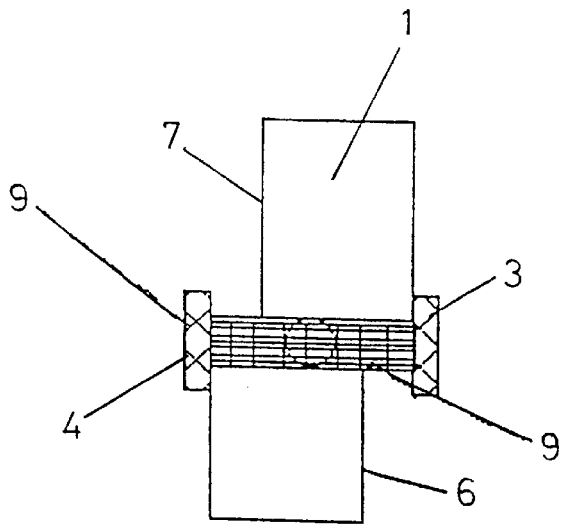
FIG. 2 is a corresponding view to that in FIG. 1, but with the sound path illustrated.
Figure 3:
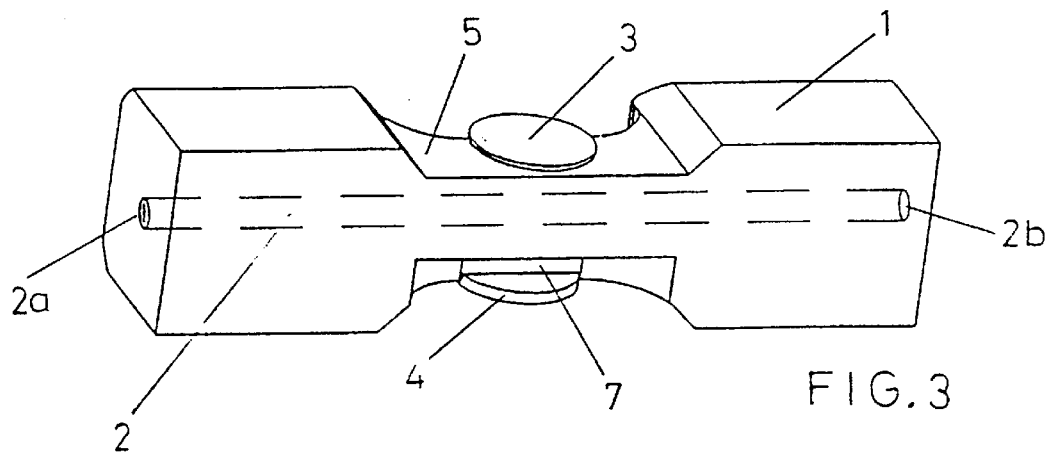
FIG. 3 is a schematic perspective view of an embodiment of the apparatus according to the invention, substantially corresponding to the embodiment shown in FIGS. 1 and 2.

The bubble detection apparatus shown in FIGS. 1 to 3 is primarily intended to be used for the detection of air/liquid in passages for liquid chromatography, but it may, of course, also be used in other applications where gas bubbles (or other inhomogeneities) in a liquid flow are to be detected. The apparatus comprises a housing or cell body 1 provided with a liquid through-passage 2 with an inlet and an outlet 2a, 2b (FIG. 3) designed to be connected to the liquid flow system in question. The cell body 1 is suitably made in hard plastic, e.g. PEEK. The passage dimension (cross-sectional diameter) is for the contemplated liquid chromatography application typically in the range of 1 to 5 mm. Two ultrasonic transducers 3, 4, here discs of piezoelectric crystal—so-called piezotransducers—are mounted to the cell body opposite each other on either side of the liquid passage 2. As will be explained in more detail below, one transducer is used as sender and the other as receiver in cooperation with an electronic control circuit. For best performance, the piezoelectric transducers are used at their resonance frequency, which depends inter alia on the thickness of the crystal disc. For a combination of two discs having a diameter of 5 mm and a thickness of 0.5 mm, for example, the resonance is at about 4 MHz.

In the embodiment shown in FIG. 3, the two transducers 3, 4 are mounted to a waist portion 5 of the cell body in order to reduce the distance between the transducer and the liquid passage.

The cell body 1 is further provided with two opposed cuts or recesses 6, 7, one recess 6 being provided between one transducer 3 and the liquid passage 2, and the other recess 7 being provided between the other transducer 4 and the liquid passage 2. The recesses 6, 7 extend vertically in opposite directions in FIGS. 1 and 2 to the level of the respective outer edge of the passage 2, these outer edges being indicated by sight lines 8a, 8b in FIG. 1. Together, the two vertically and horizontally opposed recesses 6, 7 function as a shielding or "diaphragm" for the sound waves emitted from the sending transducer, so that the sound transmitted between the transducers 3, 4 follows a route which in the vertical direction in FIGS. 1 and 2 essentially is restricted to the extension of the liquid passage. The sound path obtained is indicated in FIG. 2 by reference numeral 9. As is readily seen, this shielding or guiding of the ultrasound results in that substantially all sound energy that is detected by the receiving transducer has passed through the liquid passage 2. From the viewpoint of sound guiding or shielding, it is, of course, advantageous if the recesses 6, 7 in the horizontal direction in FIGS. 1 and 2 extend essentially all the way from the respective transducer 3, 4 to the passage 2, as shown in FIGS. 1 and 2.

Due to the fact that the two recesses 6, 7, when viewed vertically in FIGS. 1 and 2, are positioned on different sides of the liquid passage 2, the cell body will maintain a considerable twisting or torsional strength. The material thickness around the passage 2, and not least in the waist portion 5 in the embodiment of FIG. 3, is, of course, adjusted to the mechanical requirements for each specific application. Optionally, the recesses 6, 7 may be filled with a material having a high acoustic impedance.

Figure 4:
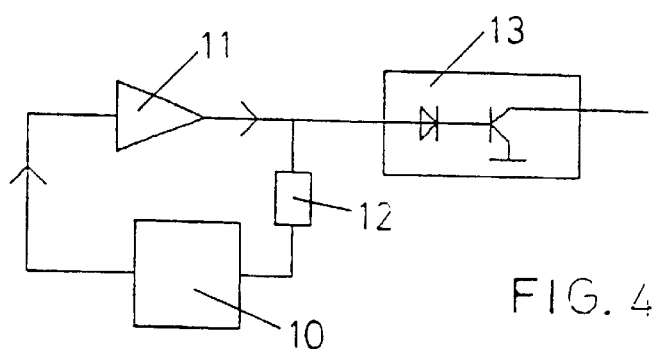
FIG. 4 is a schematic circuit diagram for electronic processing of the transducer signal from an apparatus according to the invention.

As emphasized previously, the fact that the liquid passage 2 dominates the area that the emitted ultrasound passes through the cell results in that a great and reliable difference between the respective sound intensities detected for liquid and gas, usually air, is obtained. This causes in turn that the electronic circuit that is necessary for driving the detector cell may be made very small. A schematic example of such a circuit is shown in FIG. 4.

In this circuit, the sending transducer of a detector cell of the type described above, here designated by reference numeral 10, is connected to the input of an amplifier 11, while the receiver of the detector cell 10 is connected to the output of the amplifier via a resistor 12. The amplifier output is also connected to an output driver stage 13 comprising a rectifier and a transistor. The magnitude of the resistor 12 is selected for adjusting the amplified cell detector signal to a desired level. The output signal from the driver stage 13 is then conducted to a suitable display device, or is used as control signal in an automated system.

As appears from the above, the bubble detection apparatus described provides a robust unit which is suitable for small liquid passage dimensions, gives a reliable detection of air bubbles, and only requires a simple control electronic circuitry simultaneously as it is easy to handle and manufacture (one-piece cell body).

The invention is, of course, not restricted to the embodiments specifically described above and illustrated on the drawings, but may be changed and modified in many ways within the general inventive concept as defined in the following claims.

What is claimed:

1. An apparatus for detecting inhomogeneities, particularly gas bubbles, in a liquid flow, which apparatus comprises:
    a one-piece housing (1) of a material that is transmissive to ultrasound,
    a liquid passage (2) extending through the housing (1), inlet and outlet means (2a, 2b) on the housing (1) for connecting the liquid passage (2) to the liquid flow, and ultrasonic transducer means (3, 4) on the housing on each side of the liquid passage (2), a sending transducer means being arranged as sender and a receiving transducer means being arranged as receiver, with the liquid passage (2) positioned in the sound transmission path between the sender and the receiver, whereby inhomogeneities in the liquid flow can be detected based on the emitted ultrasound energy that is received by the receiver, characterized in that the housing (1) has two opposed recesses (6, 7), one on the sender side of the liquid passage (2) and one on the receiver side thereof, which recesses extend in a direction perpendicular to the sound transmission path (9) as well as to the liquid passage (2), and extend on opposite sides of the sound transmission path (9) substantially to the level of the respective outer edge (8a, 8b) of the liquid passage (2), in order to together, by shielding, guide the ultrasound transmission between the sending transducer means and the receiving transducer means so that the ultrasound transmission takes place substantially through the liquid passage (2).

2. The apparatus according to claim 1, characterized in that the recesses (6, 7) in the sound transmission direction extend from each ultrasonic transducer means (3, 4) to the vicinity of the liquid passage (2).

3. The apparatus according to claim 1, characterized in that the housing (1) is made of hard plastic.

4. The apparatus according to claim 1, characterized in that the recesses (6, 7) are filled with a material of high acoustic impedance.

5. A system for detecting inhomogeneities, particularly gas bubbles, in a liquid flow, characterized in that the system comprises an apparatus according to claim 1, and an electric circuit for driving and signal processing.

* * * * *